United States Patent [19]

Chamoun

[11] Patent Number: 4,924,875
[45] Date of Patent: May 15, 1990

[54] CARDIAC BIOPOTENTIAL ANALYSIS SYSTEM AND METHOD

[75] Inventor: Nassib G. Chamoun, W. Roxbury, Mass.

[73] Assignee: Biometrak Corporation, Cambridge, Mass.

[21] Appl. No.: 107,419

[22] Filed: Oct. 9, 1987

[51] Int. Cl.$^5$ ............................................... A61B 5/04
[52] U.S. Cl. ................................... 128/696; 128/702; 128/703; 128/704
[58] Field of Search ............... 128/696, 702, 703, 704, 128/705, 901

[56] References Cited

U.S. PATENT DOCUMENTS

| | | | |
|---|---|---|---|
| 3,499,124 | 3/1970 | Wortzman | 128/696 |
| 4,336,810 | 6/1982 | Anderson et al. | 128/702 |
| 4,665,485 | 5/1987 | Lundy et al. | 128/702 |
| 4,732,158 | 5/1988 | Sadeh | 128/702 |
| 4,742,831 | 5/1988 | Silvian | 128/696 |

OTHER PUBLICATIONS

J. N. Hershleb. Signal Analysis of Ventricular Fibrillation.
N. G. Chamoun. Bispectral Analysis of Phase Lockin in the R—R Interval Series.
N. G. Chamoun. Autonomic Control of Phase Locking in the R—R Interval Series as Assessed by the Bispectrum.
N. G. Chamoun. Bispectral Properties of the R—R Interval Time Series.
Brillinger, D. R. An Introduction to Polyspecta.
Huber, P. J., Statistical Method for Investigating Phase Relations in Stationary Stochastic Processes.
Tyron, P. V., The Bispectrum and Higher-Order Spectra: A Bibliography.
Nikias, C. L., Bispectrum Estimation: A Digital Signal Processing Framework.
Kleiner, N., Analysis of the Interelations Between Frequency Bands of the EEG by means of the Bispectrum.
Dumermuth, G., Analysis of the Interrelations Between Frequency Bands of the EEG by means of the Bispectrum.
Barnett, T. P., Bispectrum Analysis of Electroencephalogram Signals During Walking and Sleeping.
Susumum, T., Analysis of Wave Shapes of Alphas Wave on EEG by means of the Bispectrum.
Whitton, J. L., Genetic Dependence of the Electroencephalogram Bispectrum.
Raghuveer, M. R., Bispectrum Estimation: A Parametric Approach.

(List continued on next page.)

Primary Examiner—Francis Jaworski
Assistant Examiner—George Manuel
Attorney, Agent, or Firm—Hale and Dorr

[57] ABSTRACT

Disclosed is a cardiac biopotential analysis system and method for detecting, in a noninvasive manner, the degree of myocardial ischemia and the amount of cardiac electrophysiologic stability present in a subject. A suitable body surface electrode acquires the signal from a region of interest. The body surface electrocardiographic signals are then amplified, digitized and transmitted to a host computer where an arrhythmia free QRST complex template is chosen interactively. Using cross-correlation, 50 subsequent complexes that mask the template are extracted. A Fast Fourier Transform (FFT) is then performed on every beat. The FFT results of every QRST are used to produce a bispectral complex and real triple product arrays. Each point in these arrays is then averaged over the 50 previously acquired QRST complexes. The magnitude of each averaged point in the complex triple product arrays is then squared to produce a bispectral density array, which when divided by the complex real triple product array forms a bicoherence array. The bicoherence array provides a figure of merit for the detection and quantification of myocardial ischemia in the region probed by that lead. The array also provides a quantification of cardiac electrical properties.

25 Claims, 10 Drawing Sheets

OTHER PUBLICATIONS

Teichholz, L. E., et al., The Cardiointegram: Detection of Coronary Artery Disease in Males with Chest Pain and a Normal Resting Electrocardiogram.

Simson, M. Use of Signals in the Terminal QRS Complex to Identify Patients with Ventricular Tachycardia after Myocardial Infarction.

Cain, M. E. et al., Fast-Fourier Transform Analysis of Signal-Averaged Electrocardiograms for Identification of Patients Prone to Sustained Ventricular Tachycardia.

Nolle, F. M. A Clinical Computer System for Monitoring EKG Rythm.

Nolle, F. M. et al., The ARGUS/H System for Rapid Analysis of Ventricular Arrhythmias.

Meade, C. N., et al., ARGUS Algorithm Development.

Oliver, G. C., et al., Detection of Premature Ventricular Contractions with a Clinical System for Monitoring Electrocardiographic Rhythms.

Balm, G., Crosscorrelation Techniquies Applied to the Electrocardiogram Interpretation Problem.

Automatic Reel Time Arrhythmia Monitoring in the Intensive Coronary Care Unit. American Journal of Cardiology.

Spitz, A. L., et al., Ambulatory Arrhythmia Quantification by a Correlation Technique.

Spitz, A. L. et al., Automated Family Classification in Ambulatory Arrhythmia Monitoring.

Drawing No.: 261101-873. Name: Pre Amp Iso.

Patient Safety. Hewlett-Packard.

Solar Cells Make Monitoring Safe.

Holmer, N. G., Isolation Amplifier Energized by Ultrasound.

Klijn, J. A., The Isolation Amplifier, An Interface Between EEG Recorder and Data Processor.

Moseley, H., et al., Removal of AC Interface from the Electrocardiogram.

Fig. 4
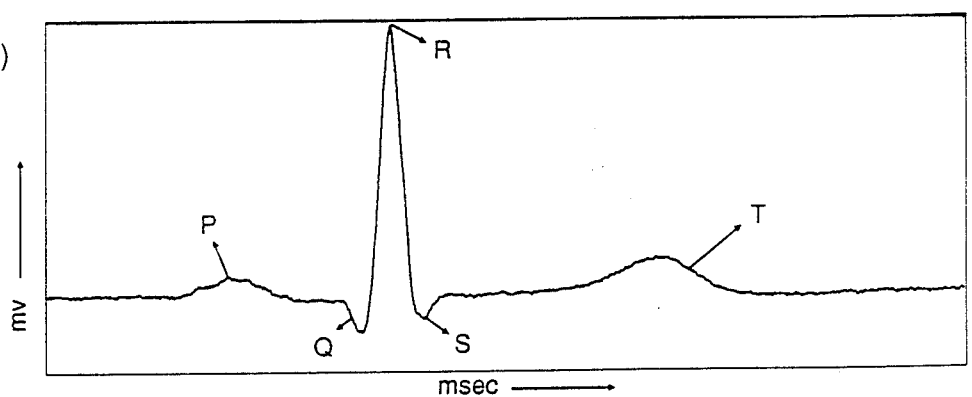
Fig. 4(a)
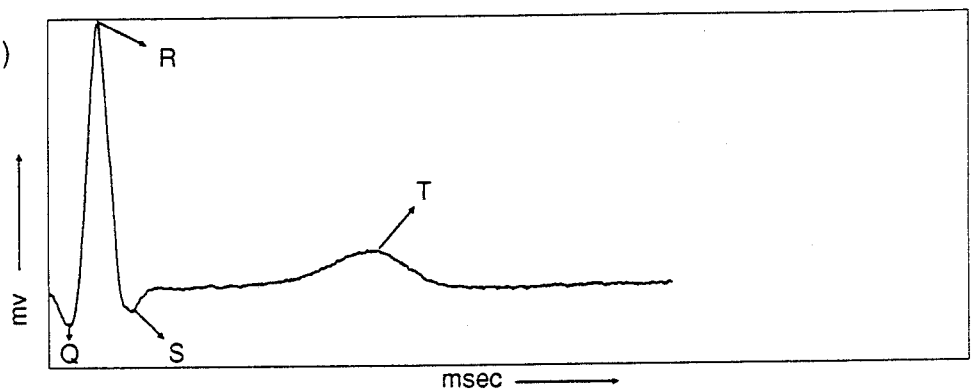
Fig. 4(b)
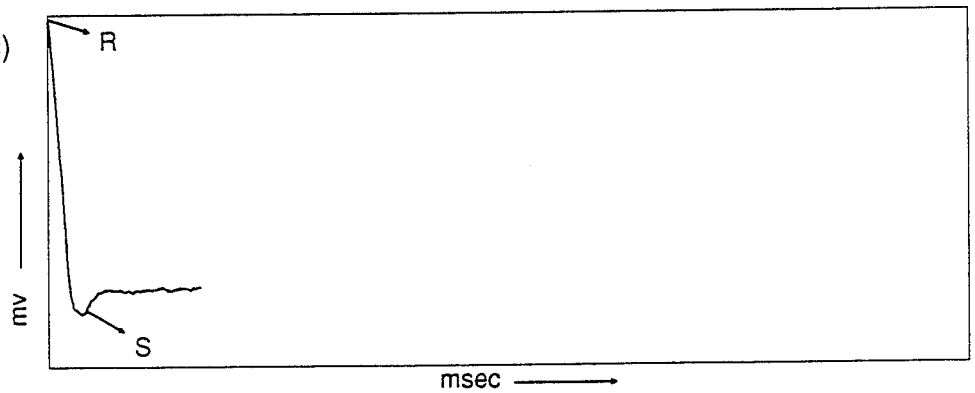
Fig. 4(c)
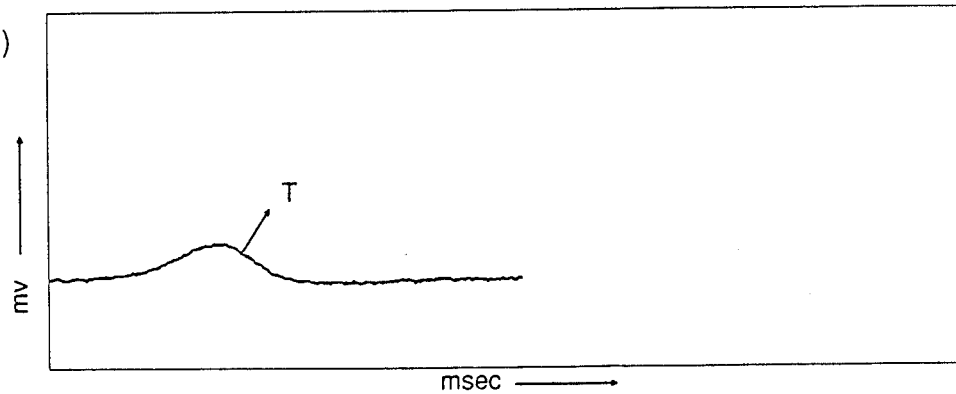
Fig. 4(d)

Fig. 5
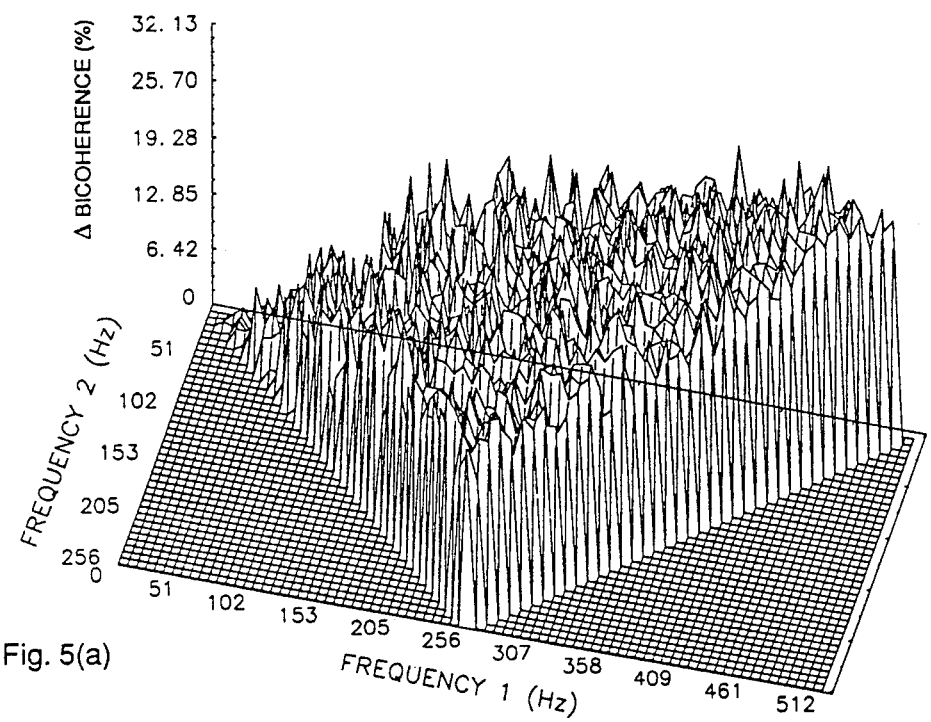
Fig. 5(a)
Sample Bicoherence Difference Array
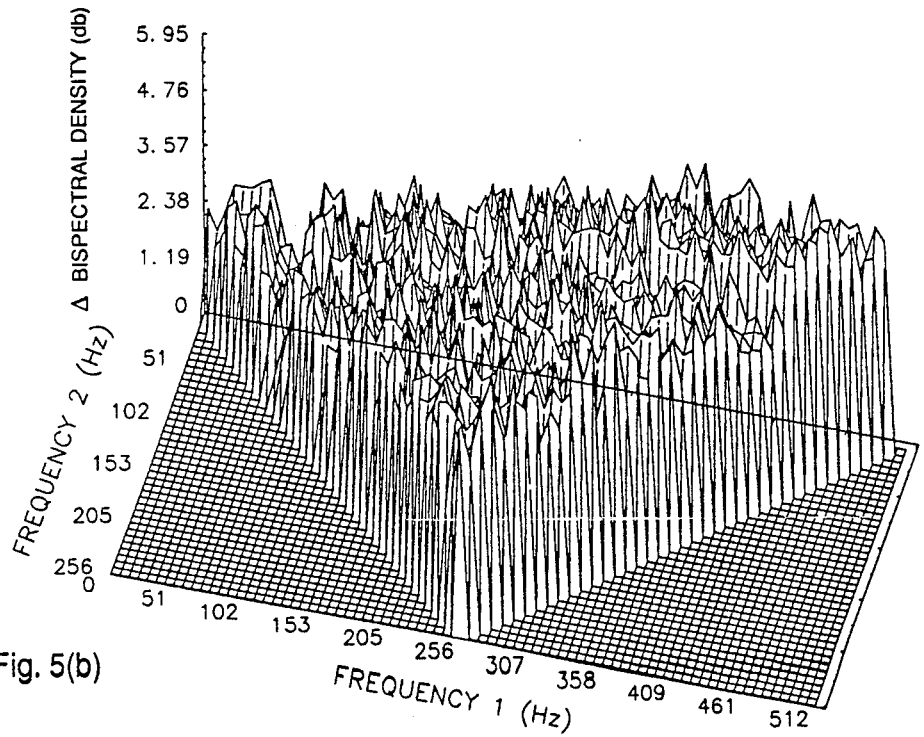
Fig. 5(b)
Sample Bispectral Density Difference Array

CARDIAC BIOPOTENTIAL ANALYSIS SYSTEM AND METHOD

BACKGROUND OF THE INVENTION

The present invention relates to a cardiac biopotential analysis system and more particularly to a cardiac biopotential analysis system utilizing bispectral analysis to determine in a noninvasive manner, important myocardial physiologic properties.

Over the years many approaches have been utilized to extract information from the electrocardiogram regarding ischemia, propensity to ventricular tachycardia and other disorders in the heart which affect cardiac electrical activity. Most of these techniques have been restricted to analysis in the time domain (e.g., Cardiointegram ®, ST segment analysis, signal averaged late potentials). More recently, analysis involving quantification of the frequency content of portions or of all of the QRST complex as determined by the Fourier transform of a second order correlation function (better known as the power spectrum) has been utilized. These techniques have generally been found to work for certain purposes but not for others or have been found to generate figures of merit with poor positive predictive capability for the disorder evaluated.

Since cardiac signals arise from the discharge of hundreds of thousands of electrically active cells, these potentials produce a complicated resultant electrical signal. Imbedded in that signal is information regarding frequency content, non-linearities and phase relationships, all arising from the complex conduction dynamics that take place between the various regions of the cardiac tissue. When transmitted to the surface, where the cardiac signal is picked up by the electrodes, the cardiac signal undergoes alteration in morphology and frequency content as a result of factors including body fat content, rib cage size, and position of the heart relative to the lungs. All these variables lead to challenging signal processing problems that conventional time and frequency domain analyses fail to address, since information regarding non-linearities and phase relationships is suppressed.

The electrical signal of the normal heart is a composite of the multitude of individual signals which are repetitively active in a relatively synchronized, organized pattern. Coronary artery disease may lead to episodes of ischemia, which alter the normal pattern of electrical activity of the heart. The conventional scalar ECG displays ischemia as a shift in the ST segment, but this technique is not sensitive or specific enough to allow a reliable noninvasive diagnosis of coronary disease.

In those patients with coronary atherosclerosis, especially in conjunction with heart damage and scarring; there is an enhanced risk of sudden cardiac death from ventricular arrhythmias. Although ventricular tachycardia (VT) can often be the initiating arrhythmia, the terminal arrhythmia is ventricular fibrillation (VF). The propensity for VF is determined by the degree of heterogeneity or disorganization of cardiac electrical conduction and repolarization. Such heterogeneity, however, cannot be discerned using conventional scalar electrocardiography. Therefore, the ability to predict noninvasively, reliably and quantitatively this propensity for VF would be highly desirable, and the further ability to predict VT, an initiator of VF, would enhance overall predictive power.

Reentrant circuits capable of sustaining ventricular tachyarrhythmias require heterogeneous conduction pathways, a substrate commonly occurring in individuals with myocardial infarction. Delayed ventricular activation is often seen as an electrophysiological consequence of myocardial infarction. The detection of delayed ventricular potentials identifies a subset of patients at higher risk for ventricular tachyarrhythmias, as compared to those patients not having late potentials. Although the mere presence of late potentials is highly sensitive for ventricular tachyarrhythmias (i.e., it correctly detects many of those who will develop ventricular tachyarrhythmias), it is not highly specific (i.e., it falsely detects many of those who will not develop ventricular tachyarrhythmias).

It is therefore a principal object of the present invention to provide a noninvasive system and method for diagnosing coronary disease.

A further object of the present invention is to provide a noninvasive system and method for the detection and quantification of myocardial ischemia.

Another object of the present invention is to provide a noninvasive system and method for the detection and quantification of cardiac electrical instability.

It is still another object of the present invention to provide a noninvasive system and method for quantifying heterogeneity in conduction and repolarization.

A still further object of the present invention is to provide a cardiac biopotential analysis system and method which obtains information in a noninvasive fashion that is comparable to information obtained through invasive electrophysiologic testing and coronary angiography.

SUMMARY OF THE INVENTION

The cardiac biopotential analysis system and method of the present invention detects, in a noninvasive manner, the degree of myocardial ischemia and the amount of cardiac electrophysiologic stability present in a subject. A suitable body surface electrode acquires the signal from a region of interest. The body surface electrocardiographic signals are then amplified, digitized and transmitted on a serial RS232C line to a host computer where a sinus normally conducted QRST complex template is chosen interactively. Using cross-correlation, a preselected number of subsequent complexes or records that match the template are extracted. A Fast Fourier Transform (FFT) is then performed on every beat. The FFT results of every QRST are used to produce a bispectral complex triple product array and a bispectral real triple product array. The arrays from all of the preselected number of records are added point by point and then divided by the preselected number to create an average complex triple product array and a real triple product array. The magnitude of each averaged point in the complex triple product arrays is then squared to produce a bispectral density array, which when divided by the real triple product array forms a bicoherence array. The bicoherence array for that ECG lead is displayed on a video terminal or plotted on paper. This array provides a figure of merit for the detection and quantification of myocardial ischemia in the region probed by that lead. The array also provides a quantification of cardiac electrical properties. In particular the array quantifies the contribution to overall cardiac electrophysiologic stability provided by the region probed by that lead. This information enables the prediction of the likelihood of the subject suffering ventricular tachycardia or ventricular fibrillation. The array also permits the identification of abnormalities of accessory pathway atrioventricular conduction as well as abnormalities in intraventricular conduction. These capabilities are present whether the entire QRST complex is analyzed or only a pre-selected portion of the QRST complex, such as the initial 40 milliseconds or the terminal 40 milliseconds of the QRS complex, is examined.

These and other objects and features of the present invention will be more fully understood from the following detailed description which should be read in light of the accompanying drawings in which corresponding reference numerals refer to corresponding parts throughout the several views.

BRIEF DESCRIPTION OF THE DRAWINGS

FIG. 4A is a diagram of a sample QRST complex utilized by the system and method of the present invention;

FIGS. 4B–4D are diagrams of possible extraction templates utilized for bispectral analysis by the method and system of the present invention;

FIGS. 5(a) and 5(b) are diagrams of sample simulated three-dimensional plots of a difference bicoherence array and a difference bispectral array respectively;

DETAILED DESCRIPTION OF THE PREFERRED EMBODIMENTS

The present invention utilizes the Fourier transform of the third order autocorrelation function, known as the bispectrum, which is an analytic process that quantifies non-linearities and phase relationships intrinsic to any waveform. Bispectral decomposition of the cardiac signal produces a result independent of rib cage size, body fat content, and position of the heart relative to the lungs. This independent result occurs because the bispectral process involves an evaluation of the relational component of the fundamental constituents comprising a signal, without regard for their absolute magnitudes. Since the altered phase relationships among ischemic cardiac cells are reflected in alterations in the phase relationships of the frequency components of the ECG signal, bispectral analysis, by providing a quantitative index of these relationships, measures the alteration in the "fine fingerprint" imbedded in the structure of the surface signal. By providing this quantitative fingerprint, the present invention provides a unique quantitative approach to the diagnosis of ischemia and other coronary malfunctions.

Figure 1:
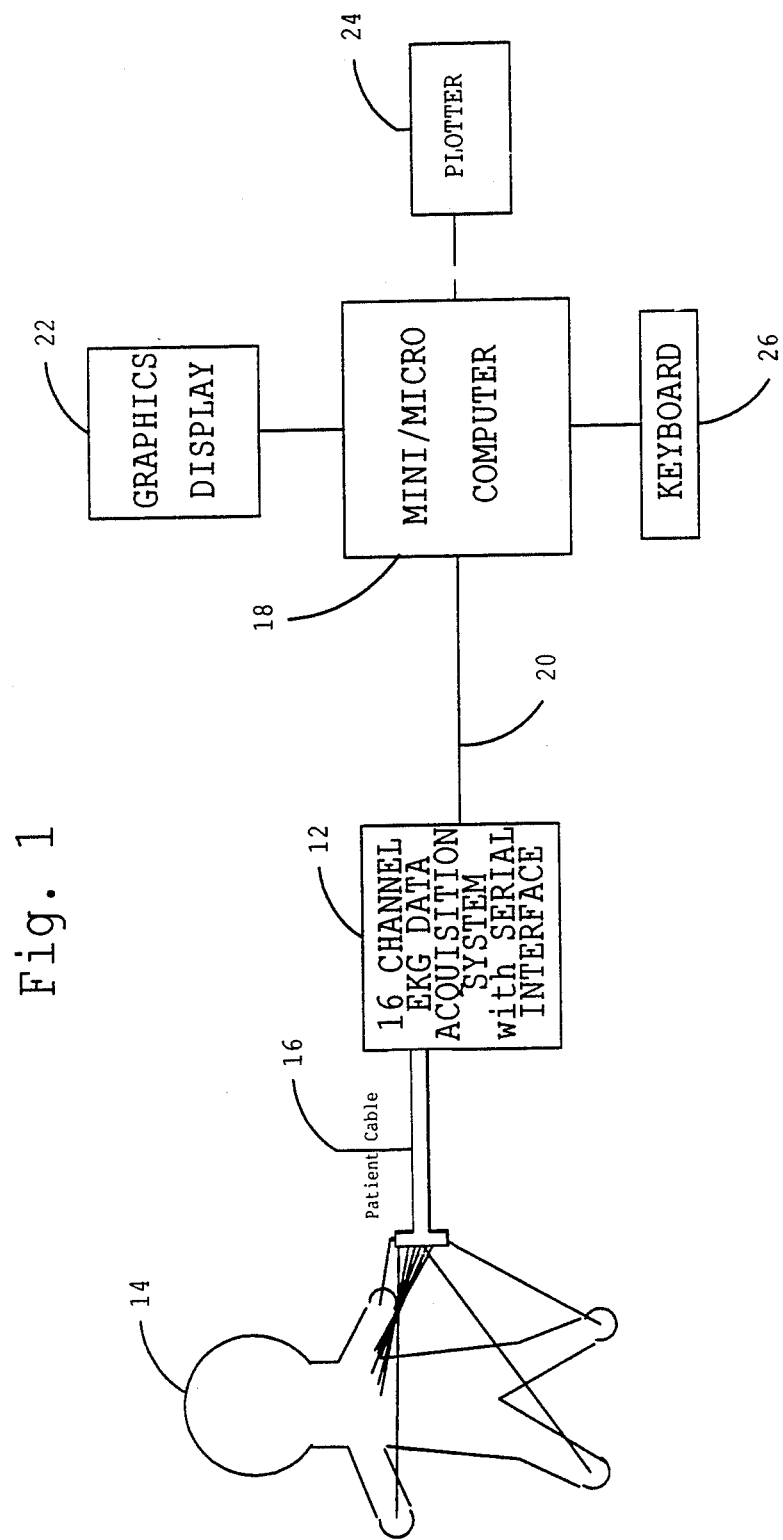
FIG. 1 is a schematic diagram of the components of the cardiac biopotential analysis system of the present invention.

Referring to FIG. 1, the bispectral analysis system 10 of the present invention includes a sixteen channel EKG data acquisition system 12 having a serial port. The electrocardiograph (ECG) leads I, II, III, AVR, AVF, AVL, V1, V2, V3, V4, V5, V6, V7, V8, V9, V10, X, Y and Z are connected to a patient 14, and signals pass through cable 16 to the sixteen channel data acquisition system 12. As will be described in greater detail below, the data acquisition system 12 amplifies and digitizes the EKG waveforms and sends the digitized data to a microcomputer 18 via a serial port over line 20 for analysis. In addition, the serial line 20 can be used to download programs.

The microcomputer 18 analyzes the serial data stream and calculates the bispectrum which is displayed on the graphics display 22. Hard copy output of the bispectrum waveform is available on plotter 24 which is also connected to microcomputer 18. Interaction between the acquisition and analysis process in the system is provided by means of a keyboard 26 with feedback on the graphics display 22.

Figure 2:
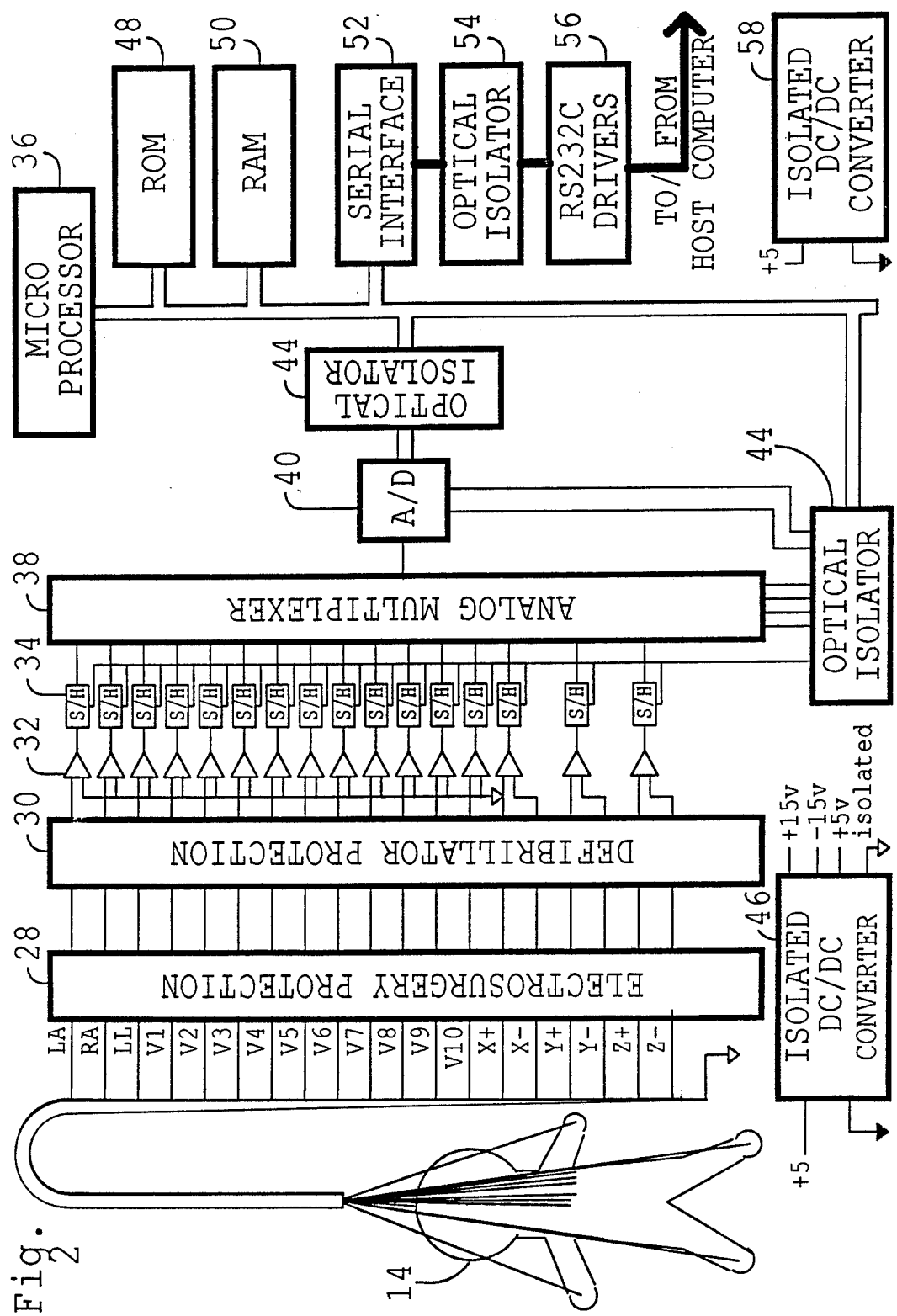
FIG. 2 is a schematic diagram of the sixteen channel EKG data acquisition system, utilizing a serial interface, of the cardiac biopotential analysis system shown in FIG. 1.

Referring now to FIG. 2 which shows the sixteen channel data acquisition system 12 in greater detail, the EKG surface potential from the patient 14 passes through an electrosurgery protection circuit 28 and a defibrillator protection circuit 30 before being transmitted to an amplifier circuit 32 that includes an amplifier for each channel. The electrosurgery protection circuit 28 includes a radio frequency (rf) filter which limits the rf current to the patient leads, and thus protects the patient 14 from rf burns and protects the amplifiers in amplification circuit 32 from excessive voltage and/or current. The defibrillator protection circuit 30 limits the voltage to the amplifier circuit 32 to a safe level (on the order of ±15 volts) when a defibrillator is applied to the patient and discharged (on the order of 5 kilovolts). The defibrillator protection circuitry also limits the current through patient leads during a defibrillator discharge.

The output of each of the 16 channels of amplification is fed into a respective one of the 16 sample-and-hold circuits 34 which are under program control of a microprocessor 36. The outputs of the sample-and-hold circuits are multiplexed by multiplexer 38 and digitized by 16 bit analog-to-digital converter 40 at a rate of 1024/sec. The output of the analog-to-digital converter 40 is optically coupled to a data bus 42 with an optical isolator 44. All control lines to the sample-and-hold circuit 34, multiplexer 38 and analog-to-digital converter 40 are optically isolated by optical isolator 45. All DC power lines going to the amplifiers 32, sample-and-hold circuits 34, multiplexer 38 and analog-to-digital converter 40 are isolated from AC mains with a DC/DC converter 46 in order to provide complete patient isolation from ground.

The microprocessor 36 controls data acquisition in the system 12. The basic control instructions for the microprocessor 36 are stored in the read only memory (ROM) 48. The random access memory (RAM) 50 is used as a buffer memory for data, and a portion of the RAM 50 can also be used as program memory when the control program is being downloaded from the host computer 18 which is connected to the system 12 by the serial line 20. The serial interface 52 operates under the control of the host computer 18. The serial interface 52 is optically coupled by optical isolator 54 to RS232C drivers 56 to provide a serial interface between the sixteen channel data acquisition system 12 and any standard RS232C serial port on a computer. The serial lines are isolated by optical isolator 54 and DC/DC converter 58 to provide increased patient safety and to protect the host computer 18 from any transients.

Figure 3:
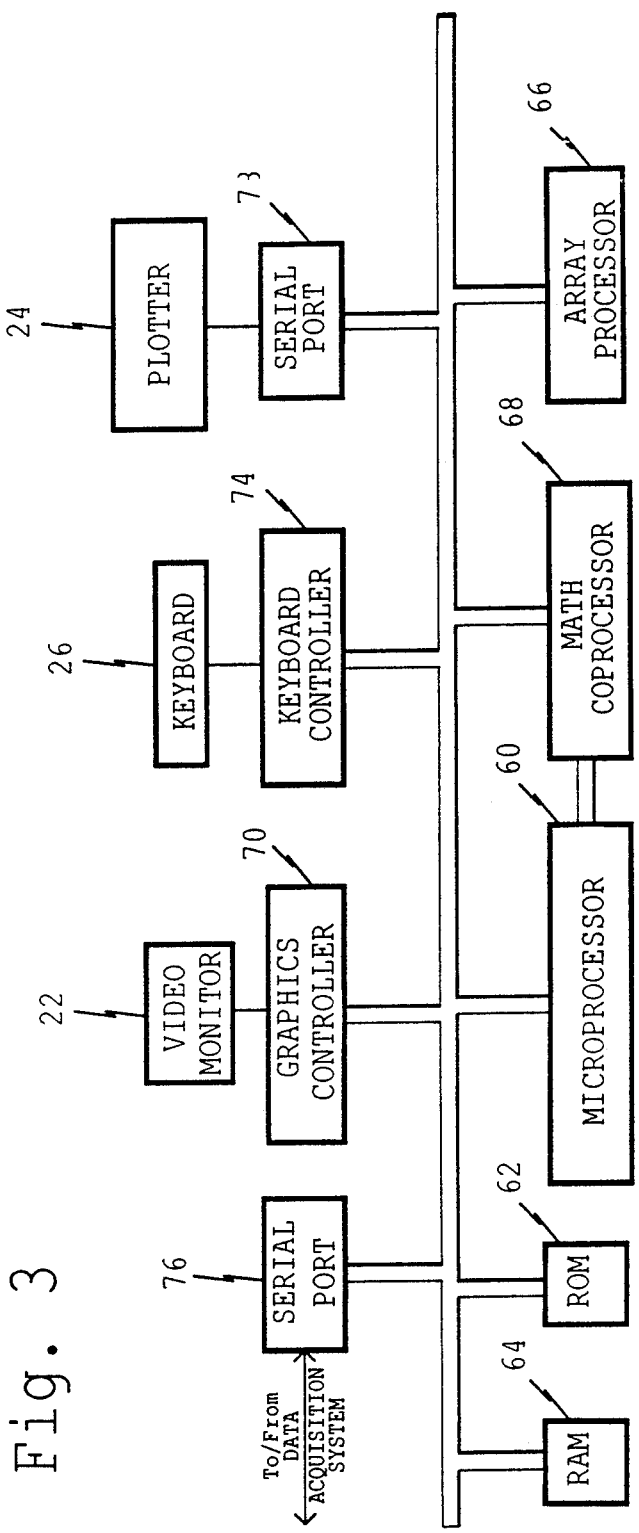
FIG. 3 is a schematic diagram of the microcomputer utilized by the cardiac biopotential analysis system of FIG. 1.

The host or microcomputer 18 of FIG. 1 is shown in greater detail in FIG. 3. The entire microcomputer system 18 runs under the control of microprocessor 60. The program memory for the microprocessor 60 is stored in ROM 62, and RAM 64 is provided for storage of intermediate data. In one preferred embodiment, the microcomputer 18 contains an array processor 66 on which complex arithmetic calculations can be performed on entire arrays of data simultaneously. The preferred embodiment also includes a math coprocessor 68 which is connected to the microprocessor 60. The math coprocessor 68 is used for scalar and graphic calculations whereas the array processor 66 is used to calculate the bispectrum and other vector computations as will be described below. The graphics controller 70 operates under program control of the microprocessor 60 and drives a video monitor 72. The keyboard controller 74 interfaces directly to the operator's keyboard 26, and operator control of the entire acquisition, analysis and display procedure is controlled by the keyboard 26 with feedback on the video monitor 22.

One serial port 76 is provided to interface with the sixteen channel data acquisition system 12. The serial port 76 can be used to send control data to the system (e.g., start acquisition) and to receive EKG data from the system, as well as to download program data to the system. Another serial port 78 is provided to drive a plotter 24 for hard copy output of the bispectrum data.

Figure 6:
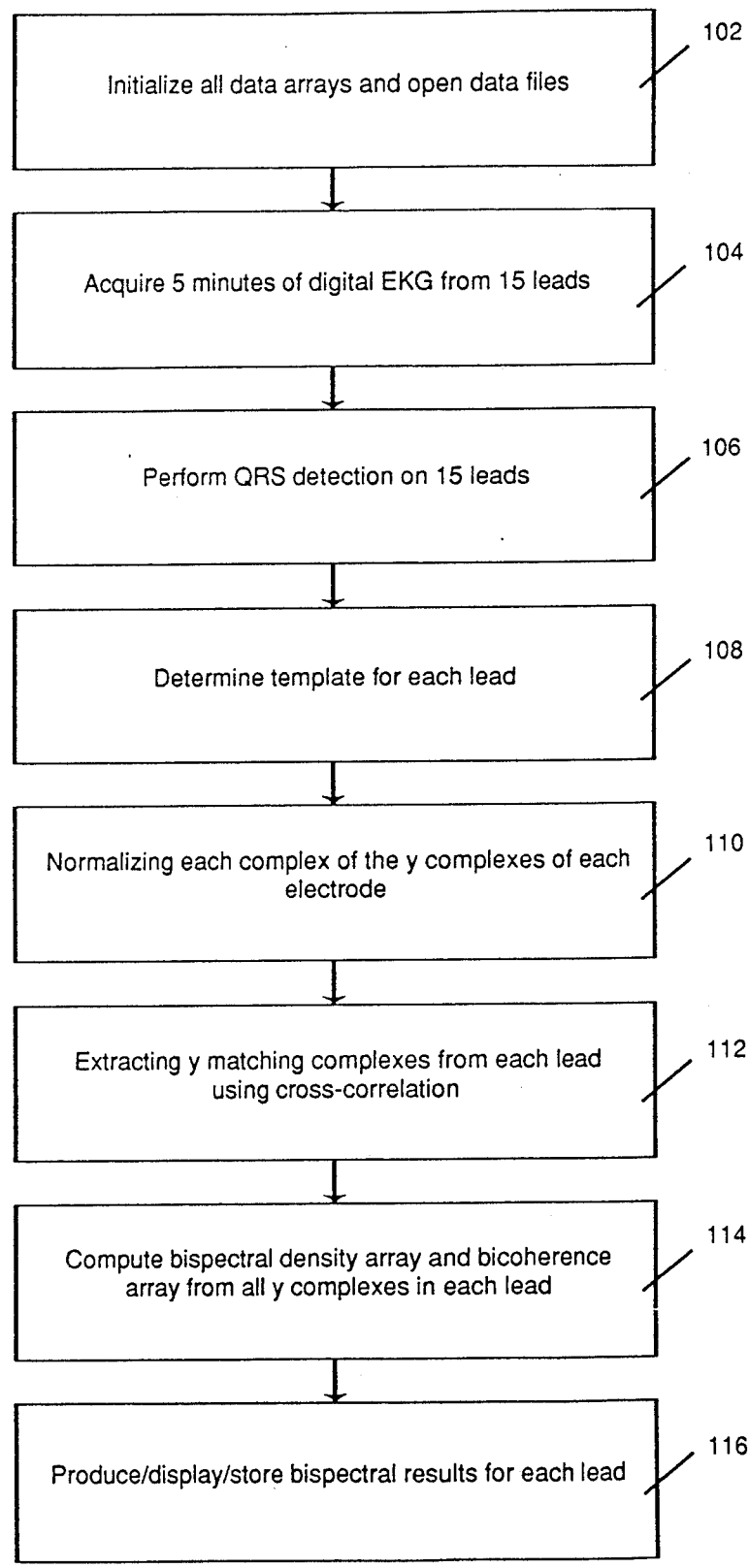
FIG. 6 is a flow chart of the operation of the system and method of the present invention for performing bispectral analysis on electrocardiographic signals.

Referring to FIG. 6, an overview of the operation of the system will now be described. After being turned on, the system initializes all data arrays and opens the relevant data files in step 102. The data arrays that are opened include arrays used to store the digitized EKG, the template, the extracted complexes and the bispectral data of each lead. The opened data files include files for final storage or comparison with existing bispectral density and bicoherence arrays.

After the system is initialized, the microcomputer 18, in step 104 acquires 5 minutes of raw electrocardiographic data (in the form of PQRST waves, as shown in FIG. 4A) from the data acquisition system 12. This raw data passes through a general purpose RS232C communication port utilizing a standard protocol, such as Kermit. In step 106 QRS detection is performed on the digital EKG of each lead using any publicly available QRS detection program (see for example "A Single Scan Algorithm for QRS-Detection and Feature Extraction," W. A. H. Engelse et al, Computers in Cardiology, IEEE Press, 1979.) In step 108 the system determines the template for interactive QRST or a portion of QRST (see FIGS. 4B-4D) for each lead in a manner that will be described below with reference to FIG. 7. In step 110, the system normalizes each potential complex of the 50 complexes of each lead. Then in step 112, after normalizing each potential complex, the system extracts 50 matching complexes from the five minutes of EKG data from each lead using cross-correlation as will be described in greater detail with reference to FIG. 8. As will be described with reference to FIG. 9 the bispectral density array and the bicoherence array for each lead is computed using the 50 complexes of that lead in step 114. Finally, in step 116 the bispectral results are produced relating to the cardiac electrical function as will be described with reference to FIG. 10.

Figure 7:
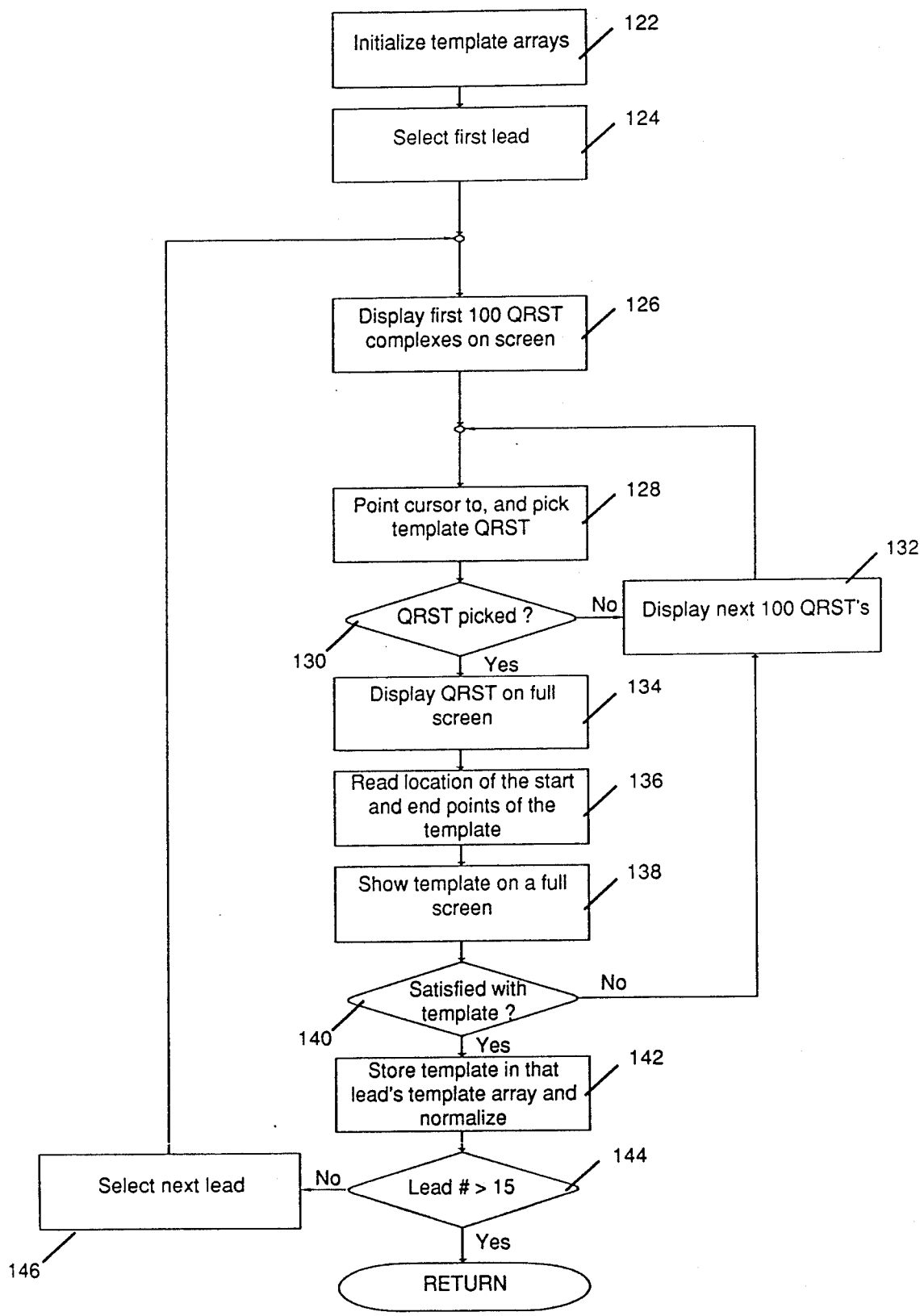
FIG. 7 is a flow chart showing the process used by the system and method of present invention for the interactive determination of the extraction template from each lead.

Turning now to FIG. 7, the process utilized by the system 10 for determining templates for each lead begins by initializing the template arrays in step 122. The determined templates are used for the extraction of 50 similar complexes from the digital EKG data of each lead. After initialization, the first lead is extracted for processing in step 124. The first 100 QRST complexes are displayed on the screen using information provided by the QRS detection program in step 126. The display graphics can be implemented by utilizing many commercially available software packages for micro and minicomputers. (For example, systems sold by IBM, Precision Visuals Corp., Microcompatibles, Inc.) From the display, the operator in step 128 picks the most artifact-free sinus QRST complex by moving the cursor to that position on the screen. Step 130 tests if a complex is picked from the displayed 100 complexes and if one is not picked, the next 100 QRST complexes is displayed in step 132. If a QRST complex is chosen, then it is displayed on the screen 22 with a time scale relative to the peak of the QRS which is set to zero in step 134. In step 136 the operator enters the location in msec of the start and end of the template, relative to the peak of the QRS. In step 138 the template is then displayed on a full screen.

In step 140, the operator decides whether he is satisfied with the chosen template and if he is not then control returns to step 126 and the next 100 QRST complexes are displayed on the screen. If the template is acceptable then it is stored in a template array for that lead in step 142 with the first point of the template stored in the first location and the rest extending over the remaining 512 (in a preferred embodiment) available locations (0.5 seconds). Prior to placing the template samples in the array, the mean is subtracted from each sample and it is then divided by the standard deviation. If the number of samples for the template is less than 512, all subsequent locations are padded with the value of the last sample in the template. Step 144 tests to determine which lead is currently being processed and if all the leads have not been considered step 146 selects the next lead in the sequence, and steps 126 through 142 are repeated for each lead.

Figure 8:
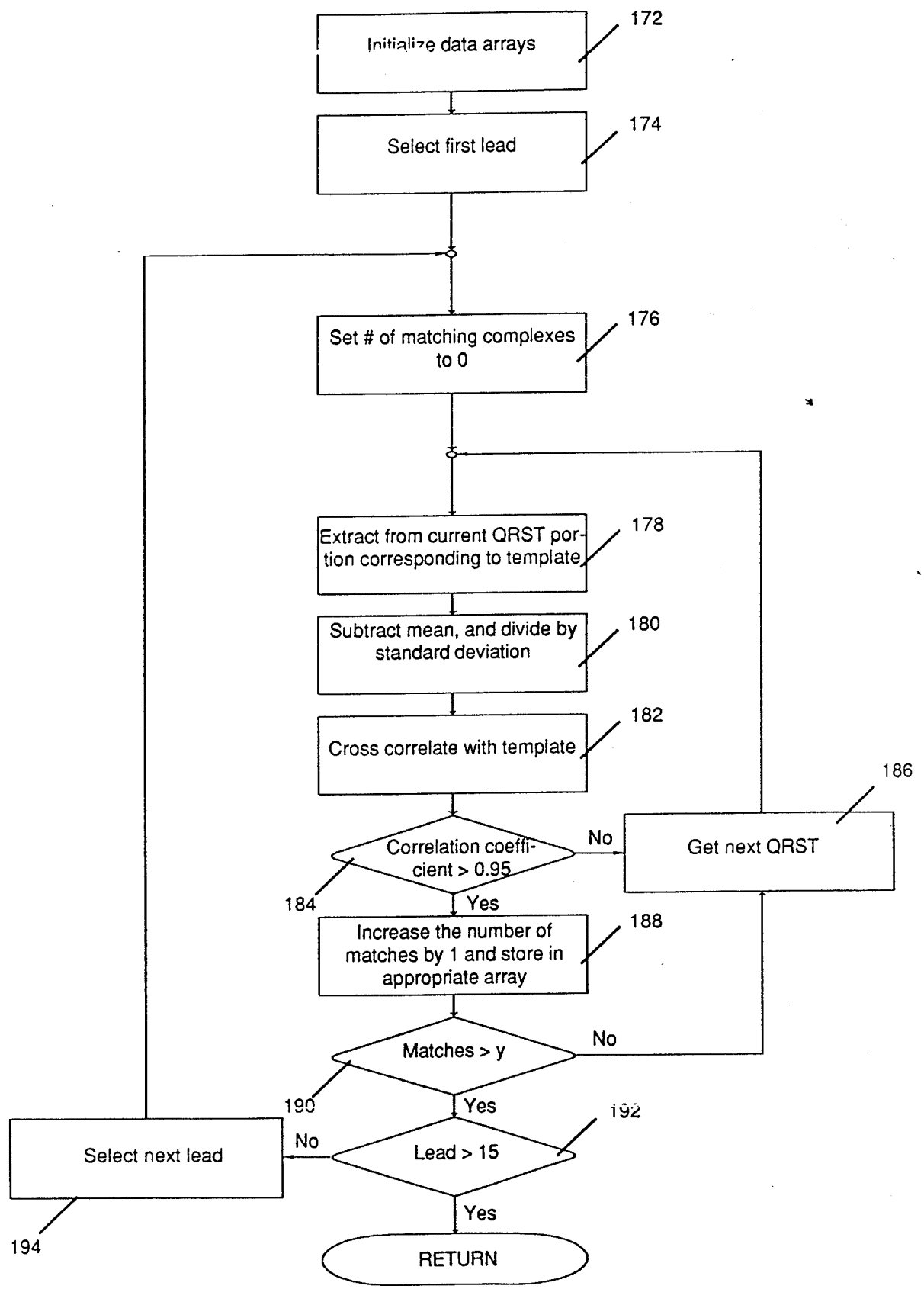
FIG. 8 is a flow chart of the process utilized by the system and method of the present invention for extracting 50 complexes from each lead to match the pre-selected template.

Referring now to FIG. 8, the process for extracting 50 matching complexes from the 5 minutes of EKG data is shown in greater detail. The selected 50 complexes from each lead must match the pre-selected template with a correlation coefficient that is greater than or equal to 0.95. Initially, in step 172 the data arrays containing the 50 complexes of each lead are initialized. In step 174 the data in the first lead is selected for processing, and in step 176 the number of matching complexes for that lead is set to 0. Using data provided by the QRS detection program, the portion of the current QRST complex that corresponds to the template is extracted in step 178. The mean of all samples in the extracted portion is subtracted from each sample, and each sample is then divided by the standard deviation of the samples in that portion in step 180. The division by the standard deviation is used to normalize the energy present in a portion to 1, making this process completely independent of the absolute amount of energy present in the signal.

A cross-correlation is carried out between the current normalized extracted portion and the template using only the non-padded values in the template array in step 182. If the cross-correlation coefficient is not greater than or equal to 0.95, which is tested in step 184, the next QRST complex is selected in step 186 and steps 178 through 184 are repeated. If the correlation coefficient is greater than or equal to 0.95, the number of matches for that lead is increased by 1, and the extracted portion is stored in the leads array for the fifty selected matches in step 188. Step 190 tests whether all the matches have been processed. If they have not, the next QRST signal is obtained in step 186, and then processing continues in step 178. If all the matches have been processed, step 192 tests to see if all the leads have been processed. If all leads have not been processed, the next lead is selected, and control returns to step 176. If all the leads have been processed, then the process for selecting the fifty complexes for each lead is concluded.

Figure 9:
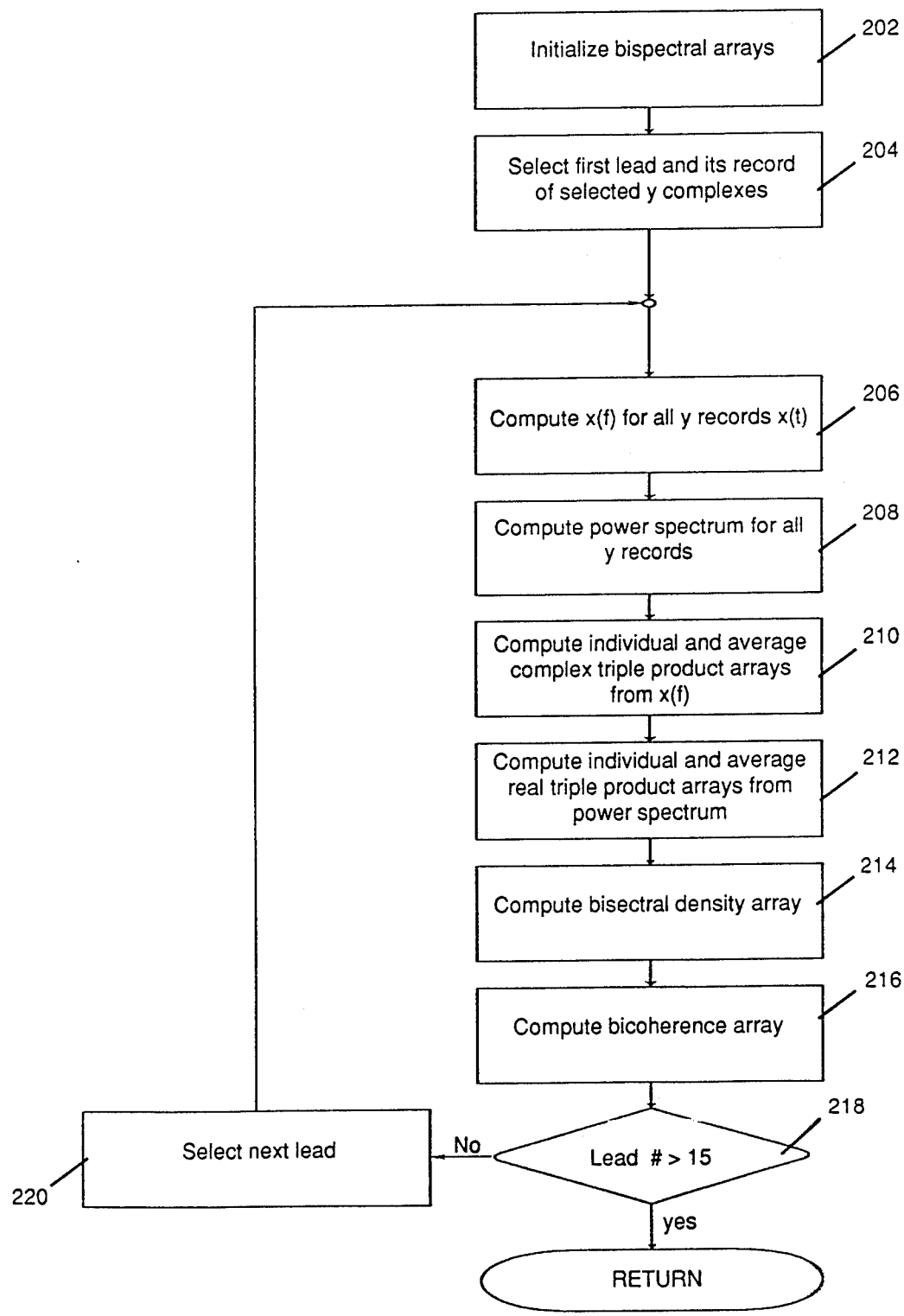
FIG. 9 is a flow chart of the process utilized by the system and method of the present invention for bispectral processing.

Referring now to FIG. 9, the process for computing the bispectrum will now be described. In step 202 the system initializes the spectral arrays, and in step 204 the data for the first lead is selected. (In the following description it is assumed that each QRST in question is a record $x_i(t)$ where $0 < i \leq 50$.) The system then computes the fast Fourier transform (FFT) $X_i(f)$ of each record or in other words for all 50 complexes in step 206. The system then computes the power spectrum $P_i(f)$ of each record or in other words for all 50 complexes in step 208. In step 210 the individual $bc_i(f_1,f_2)$ and average $BC(f_1,f_2)$ complex triple product arrays are computed for each record such that:

$$bc_i(f_1,f_2) = X_i(f_1)^* X_i(f_2)^* X_i(f_1+f_2) \quad (1)$$

$$f_1 + f_2 \leq N/2 \quad (2)$$

$$\leq f_2 \leq f_1 \quad (3)$$

where N=512 (which is the number of samples which will vary depending on the sampling rate), and where $f_1$ and $f_2$ are any frequency location in X(F) from $f = 0$ to N/2.

The average complex triple product array for all 50 complex triple products is also computed:

$$BC(f_1,f_2) = 1/50 \left[ \sum_{i=1}^{50} bc_i(f_1,f_2) \right] \quad (4)$$

In step 212 the system computes the individual $br_i(f_1,f_2)$ and average $BR(f_1,f_2)$ real triple product arrays with the real triple product for each record being specified as follows:

$$br_i(f_1,f_2) = P_i(f_1)^* P_i(f_2)^* P_i(f_1+f_2) \quad (5)$$

$$f_1 + f_2 \leq N/2 \quad (6)$$

$$0 \leq f_2 \leq f_2 \quad (7)$$

After all the individual real triple products have been computed, the average real triple product $BR(f_1,f_2)$ is calculated as follows:

$$BR(f_1,f_2) = 1/50 \left[ \sum_{i=1}^{50} br_i(f_1,f_2) \right] \quad (8)$$

Utilizing these average figures, the system in step 214 computes the bispectral density array of the average records:

$$BD(f_1,f_2) = |BC(f_1,f_2)|^2 \quad (9)$$

Finally, in step 216 the bicoherence array $R^2(f_1,f_2)$ is computed as follows:

$$R^2(f_1,f_2) = BD(f_1,f_2)/BR(f_1,f_2) \quad 0 \leq R^2 \leq 1 \quad (10)$$

The system in step 218 then tests to determine whether all the leads have been processed and if they have not the data for the next lead is selected in step 220 and control of the operation returns to step 206. If all the leads have been processed the determination of the bicoherence arrays has been concluded.

Figure 10:
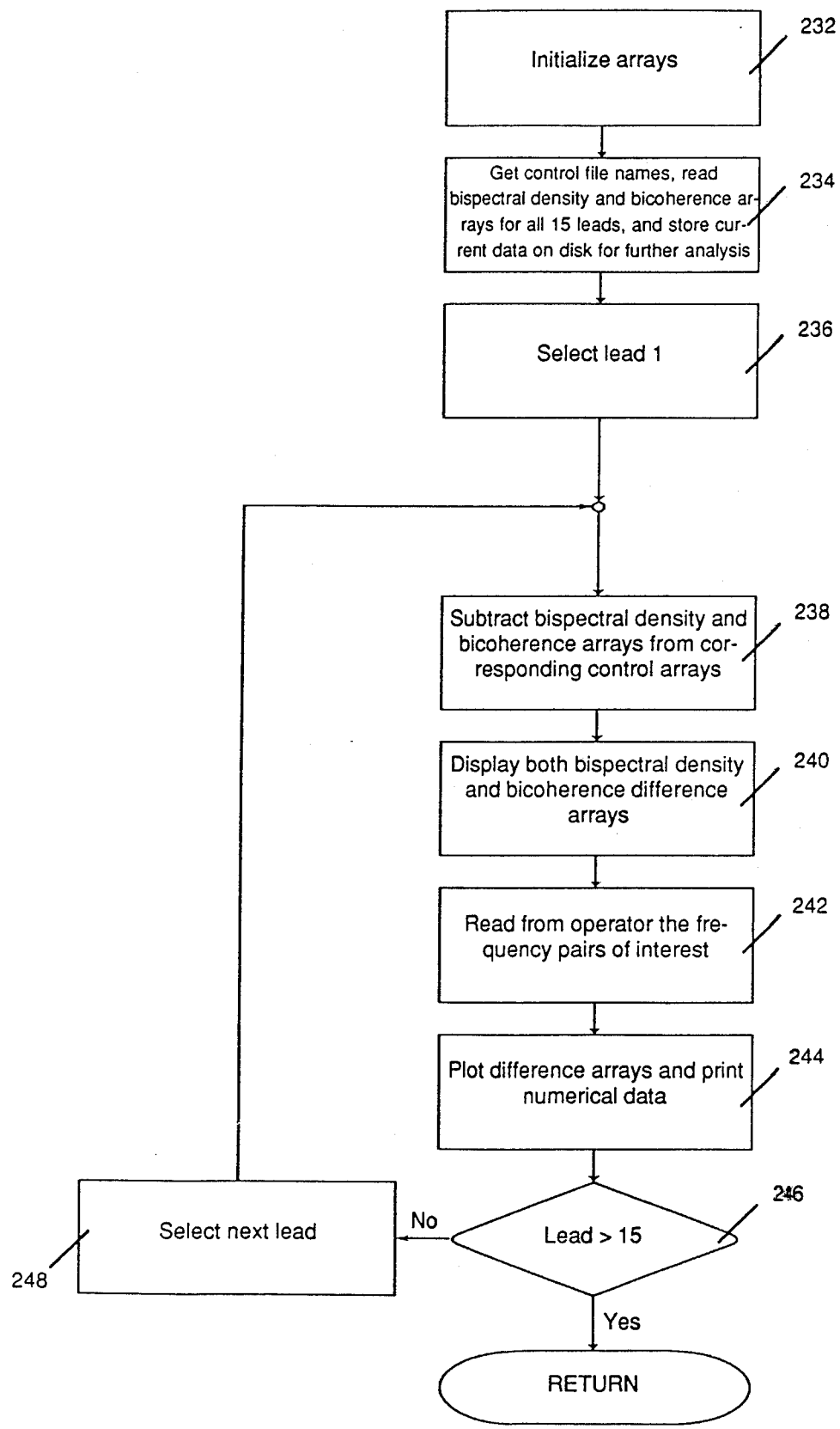
FIG. 10 is a flow chart of the process utilized by the system and method of the present invention for data analysis after all bispectral processing has been completed.

Referring now to FIG. 10, the analysis and display of the data will now be described in detail. Again, in step 232 the necessary arrays are initialized. These arrays include data arrays that contain the difference between the control bispectral values and the current bispectral values. The operator is then asked to enter into the system the file name containing the control data which can be from a group of normal subjects or preintervention data from the current subject. In step 234 both the bispectral density arrays and the bicoherence arrays for the 15 leads are retrieved from the control file in step 234 and the current arrays of the 15 leads are also stored for further off-line analysis.

Starting with lead 1 which is selected in step 236, the current bispectral density and current bicoherence arrays are subtracted from the corresponding control arrays in step 238. The absolute values of the differences are stored in a difference bispectral density array and a difference bicoherence array. The difference arrays are then displayed simultaneously on the screen in a three dimensional format for qualitative assessment of the affected frequency bands in step 240. The grids in FIG. 5 represents the difference between two bispectral density arrays or bicoherence arrays. Each point on the grid is the absolute value of the difference between the same points in the control bicoherence array and the current bicoherence array, or the control bispectral density array and the current bispectral density array. The axes are F1, ranging from 0 to 512 Hz; F2, ranging from 0 to 256 Hz; and the magnitude of the change at each point (for bicoherence, a dimensionless number ranging between 0 and 1; for bispectral density, a very large number with the unit volt$^6$). The higher the elevation in the peaks of a region representing a frequency pair band F1, F2 the greater is the electrophysiologic abnormality. Based on the visual inspection of the magnitude of the change in the various regions on the grid, the operator will choose these regions by entering the corresponding frequency pair bands. A numerical output is then produced and printed for quantitative evaluation by the operator.

The operator can then enter the values for all the frequency bands of interest in step 242. The sum of the absolute values of the changes in each selected frequency band is then computed for both the bispectral density data as well as the bicoherence data in step 244, and the printed output is generated for the quantitative assessment by the operator. In addition, a two dimensional cross-correlation between the control bispectral density and/or bicoherence arrays (and/or a subsection thereof) and the current bispectral density and/or bicoherence arrays is performed to generate a cross-correlation coefficient representing the distortion and/or deviation from the original bispectral structures. The difference arrays may also be plotted using a high resolution plotter. If all the leads have not been displayed and processed then in step 248 the data for the next lead is selected and control of the system returns to step 238. If the test in step 246 determines that all the leads have been processed, the display and data analysis portion of the system has concluded its operation.

The resultant bispectral density array and the bicoherence array are examined, and a figure of merit representing a fingerprint of the electrical activity in each lead may be displayed in a three-dimensional wire frame format.

If the bispectral computation is performed following an intervention or a procedure that alters blood flow to the heart or alters cardiac electrophysiologic stability, or both, the current bispectral density array is subtracted from and/or correlated with the control bispectral density array or any subsections thereof, and the current bicoherence array is subtracted from and/or correlated with the control bicoherence array or any subsections thereof. The control arrays are produced prior to the procedure or intervention. The greater the reduction in bicoherence and/or bispectral density and/or the lower the cross correlation coefficient in the frequency pairs in the bands between 0.05 to 100 Hz and 200 to 300 Hz, the greater the heterogeneity in conduction and repolarization. The greater this heterogeneity, the higher the likelihood of the subject suffering ventricular tachycardia or ventricular fibrillation. The greater the reduction in bicoherence and/or bispectral density and/or the lower the cross-correlation coefficient in the frequency pairs in the bands between 0 to 200 Hz, the greater the magnitude of the induced ischemia. Additionally, bispectral density arrays and bicoherence arrays from individuals with intraventricular conduction disturbances or accessory atrioventricular pathways will be reliably and quantitatively discernable from the template bispectral density array and the template bicoherence array of a population of normal individuals.

If the bispectral computation is performed in a static, steady resting state, then the bispectral density array is subtracted from a template bispectral density array, and the bicoherence array is subtracted from a template bicoherence array (the templates having been produced by averaging multiple arrays obtained from a large group of normals). The greater the reduction in bicoherence and/or bispectral density and/or the lower the cross-correlation coefficient in the frequency pairs in the bands between 0.05 to 100 Hz and 200 to 300 Hz, the greater the heterogeneity in conduction and repolarization, and the higher the likelihood of ventricular arrhythmias. The greater the change in bicoherence and/or bispectral density in the frequency pairs in the band between 0 to 200 Hz, the greater the magnitude of the steady state ischemia.

Each lead is representative of a certain region in the myocardium. Therefore, the analysis of the bispectral results accounting for amplitude variation in each lead will localize non-invasively the areas which are most susceptible to ischemia and/or which exhibit the greatest heterogeneity in conduction and repolarization.

These relationships will be true whether frequency pairs of the entire QRST complex are examined or frequency pairs of preselected portions of the QRST complex, such as the initial or terminal 40 milliseconds are analyzed.

The cardiac biopotential analysis system of the present invention as described above quantitatively represents beat to beat consistency (reproducibility) of cardiac electrical activation and repolarization. As such, normal ranges can be established for a population of human subjects. Also, alterations, whether due to disease or drugs, in the homogeneity of electrical activation and repolarization can be detected and the degree of offset can be quantified, providing an indirect quantification of the perturbing factor.

Therefore, since myocardial ischemia increases heterogeneity of conduction and repolarization, bispectral density and bicoherence in particular frequency bands will be reduced in ischemia, thereby permitting the detection of ischemia. Also, because bispectral density and bicoherence will vary inversely with degree of ischemia, bispectral density and bicoherence will provide a noninvasive quantitative measure of the amount of ischemia. In addition, because bispectral density and bicoherence, in conjunction with amplitude-domain characteristics, varies with electrode lead position on the body surface, and therefore alterations of bispectral density and bicoherence in relation to amplitude will vary with lead position, myocardial ischemia can be localized to particular regions of the heart.

Since bispectral density and bicoherence provide a quantitative, composite measure of homogeneity of activation, conduction and repolarization of cardiac tissue, and since the propensity to ventricular fibrillation integrates said cardiac electrical properties of activation, conduction and repolarization, bispectral density and bicoherence of particular frequency bands will provide a quantitative, noninvasive measure of the propensity for ventricular fibrillation. As such, bispectral density and bicoherence will allow one to distinguish between two situations, in one of which the myocardium is electrically stable and in the other of which the myocardium is electrically unstable, with the situations being indistinguishable by any other noninvasive measure currently available.

In those individuals with high frequency potentials in the terminal 40 milliseconds of the QRS complex, bispectral density and bicoherence will distinguish between those individuals with the high likelihood of ventricular tachyarrhythmias and those with the low likelihood of ventricular tachyarrhythmias who are otherwise indistinguishable by any other noninvasive measure currently available. Those individuals who develop ventricular tachyarrhythmias will have more beat-to-beat heterogeneity of conduction than those individuals who will not develop ventricular tachyarrhythmias. Therefore, bispectral density and bicoherence will be lower in those individuals having a high propensity for the development of ventricular tachyarrhythmias, and will be higher in those individuals having a low propensity for the development for ventricular tachyarrhythmias.

While the foregoing invention has been described with reference to its preferred embodiments, various alterations and modifications will occur to those skilled in the art. All such modifications and alterations are intended to fall within the scope of the appended claims.

What is claimed is:

1. A method of noninvasively detecting heart disorders that affect cardiac electrical activity, said method comprising the steps of:
    acquiring electrocardiographic signals from a surface of the body of a subject being analyzed through a surface electrode;
    determining a waveform template representing a normal QRST waveform in said subject;
    selecting a number of complexes that match said waveform template and storing said number of complexes for processing;
    computing bispectral parameters from said stored number of selected complexes;
    utilizing said bispectral parameters to quantify the contribution to overall cardiac physiologic function provided by the region probed by said surface electrode.

2. The method of noninvasively detecting heart disorders of claim 1 wherein said step of acquiring electrocardiographic signals comprises the steps of
    placing said surface electrode on a region of the body of said subject to be analyzed and detecting signals relating to cardiac activity in the region where said electrode is placed;
    amplifying signals detected by said surface electrode;
    digitized said amplified signals;
    transmitting said digitized signals in a serial stream to a processing system.

3. The method of noninvasively detecting heart disorders of claim 1 wherein said determined waveform template is a sinus QRST complex template.

4. The method of noninvasively detecting heart disorders of claim 1 wherein the step of determining the waveform template comprises:
    (a) viewing a number of QRST complexes;
    (b) if a artifact-free sinus QRST complex is displayed, selecting the most artifact-free sinus QRST complex;
    (c) if a an artifact-free sinus QRST complex is not displayed, display the next 100 complexes and repeat steps a through c until a suitable artifact-free sinus QRST complex is chosen.

5. The method of noninvasively detecting heart disorders of claim 1 wherein the step of selecting a number of complexes comprises:
    comparing each complex from a lead to said determined waveform template;
    selecting each complex matching said determined waveform template with a correlation coefficient greater than or equal to a preselected value.

6. The method of noninvasively detecting heart disorders of claim 5 wherein in said step of selecting said complexes comprises:
    extracting a portion of each complex that corresponds to said waveform template;
    subtracting the mean of all samples in the extracted portion from each sample;
    dividing each sample by the standard deviation of the samples in that portion in order to normalize the energy present in said portion to 1;
    cross-correlating the current normalized extracted portion and the template;
    selecting a sample as one of the chosen complexes if the cross-correlation coefficient is not greater than or equal to a preselected value.

7. The method of noninvasively detected heart disorders of claim 1 wherein said bispectral parameter is bicoherence and said step of computing said bispectral parameters comprises the steps of:
    performing a fast Fourier transform on each of said selected complexes;
    deriving a bispectral complex triple product array and a bispectral real triple product array from the first Fourier transforms of said selected complexes;
    averaging said points in said bispectral complex triple product array and in said bispectral real triple product array;
    squaring the magnitude of each average in the complex triple product arrays to produce a bispectral density array;
    dividing said bispectral density array by the real triple product array to obtain an array of bicoherences.

8. The method of noninvasively detecting heart disorders of claim 1 where said step of utilizing said bicoherence array to quantity the contribution to overall cardiac electrophysiological stability provided by the region probed surface electrode comprises the steps of:
    subtracting bispectral parameters from control bispectral parameters and subtracting said bicoherence array from a control bicoherence, said control bispectral parameters being produced prior to the procedure intervention;
    determining reduction in the bispectral parameter in frequency pairs in the bands between 0.05 to 100 Hz and 200 to 300 Hz;
    determining heterogeneity in conduction and repolarization on the basis that the greater the reduction in said bispectral parameter in said frequency pairs, the greater the heterogeneity;
    determining a likelihood of a subject suffering ventricular tachycardia or ventricular fibrillation based on the amount of heterogeneity.

9. The method of noninvasively detecting heart disorders of claim 1 where said step of utilizing said bispectral parameters to quantify the contribution to overall cardiac physiologic function provided by the region probed by said surface electrode comprises the steps of:
    subtracting the bispectral parameters from control bispectral parameters, said control bispectral parameters being produced prior to the procedure intervention;
    determining reduction in the bispectral parameter in frequency pairs in the bands between 0.05 to 200 Hz;
    determining heterogeneity in conduction and repolarization on the basis that the greater the reduction in the bispectral parameters in said frequency pairs, the greater the heterogeneity;
    determining a magnitude of induced ischemia on the basis of the greater the change in said bispectral parameter in the frequency pairs between 0 to 200 Hz the greater the magnitude of the induced ischemia.

10. The method of noninvasively detecting heart disorders of claim 1 wherein step of utilizing said bispectral parameters to quantify the contribution to overall cardiac physiologic function provided by the region probed by said surface electrode comprises the steps of:
    subtracting the bispectral parameters from template bispectral parameters;

determining reduction in the bispectral parameters in the frequency pairs in the bands between 0.05 to 100 Hz and 200 to 300 Hz;

determining heterogeneity in conduction and repolarization based on the reduction in the bispectral parameters in the frequency pairs and the bands between 0.05 to 100 Hz and 200 to 300 Hz;

determining a likelihood of ventricular arrhythmias based on the heterogeneity the conduction and repolarization.

11. The method of noninvasively detecting heart disorders of claim 1 wherein said step of utilizing said bispectral parameters to quantify the contribution to overall cardiac physiologic function provided by the region probed by said surface electrode comprises the steps of:

subtracting the bispectral parameters from template bispectral parameters of a population of normal individuals;

determining heterogeneity in conduction and repolarization based on the reduction in the bispectral parameters in the frequency pairs in the bands between 0.05 to 200 Hz;

determining a magnitude of steady state ischemia based on the change in the bispectral parameters in the frequency pairs in the bands between 0 to 200 Hz.

12. The method of noninvasively detecting heart disorders of claim 1 wherein said step of utilizing said bispectral parameters to quantify the contribution to overall cardiac physiologic function provided by the region probed by said surface electrode comprises the steps of:

subtracting the bispectral parameters from template bispectral parameters of a population of normal individuals;

determining beat to beat consistency in cardiac electrical activation and repolarization patterns as detected in particular frequency bands in order to detect abnormalities of ventricular activation patterns and to detect intraventricular condition defects and accessory atrioventicular pathways.

13. The method of noninvasively detecting heart disorders of claim 1 wherein said step of utilizing said bispectral parameters to quantify the contribution to overall cardiac physiologic function provided by the region probed by said surface electrode comprises the steps of:

distinguishing between those individuals with a high likelihood of ventricular tachyarrhythmias and those with a low likelihood of ventricular tachyarrhythmias on the basis that the bispectral parameters will be lower in those individuals having a high propensity for the development of ventricular tachyarrhythmias than in those individuals having a lower propensity for the development of ventricular tachyarrhythmias.

14. The method of noninvasively detecting heart disorders of claim 1 wherein said step of utilizing said bispectral parameters to quantify the contribution to overall cardiac physiologic function provided by the region probed by said surface electrode comprises the steps of:

for individuals having high frequency potentials in the terminal 40 milliseconds of the selected complex, distinguishing between those individuals with a high likelihood of ventricular tachyarrhythmias and those with a low likelihood of ventricular tachyarrhythmias on the basis that bispectral density and bicoherence will be lower in those individuals having a high propensity for the development of ventricular tachyarrhythmias than in those individuals having a lower propensity for the development of ventricular tachyarrhythmias.

15. The method of noninvasively detecting heart disorders of claim 1 wherein said step of utilizing said bispectral parameters to quantify the contribution to overall cardiac physiologic function provided by the region probed by said surface electrode comprises the steps of:

correlating said bispectral density array with a control bispectral density array in order to produce a cross-correlation coefficient, determining the reduction in the bispectral density cross-correlation coefficient in the frequency pairs in the bands between 0.05 to 200 Hz;

determining the magnitude of induced ischemia on the basis of the greater the reduction in the bispectral density cross-correlation coefficient in the frequency pairs between 0 to 200 Hz from a base cross-correlation coefficient, the greater the magnitude of the induced ischemia.

16. The method of noninvasively detecting heart disorders of claim 15 further comprising the step of:

after producing said cross-correlation coefficient, displaying the cross-correlation coefficient of the bispectral density array on a grid, said grid having an area representing a location probed by each electrode with each area containing a cross-correlation coefficient of the bispectral density array.

17. The method of noninvasively detecting heart disorders of claim 1 wherein said step of utilizing said bispectral parameters to quantify the contribution to overall cardiac physiologic function provided by the region probed by said surface electrode comprises the steps of:

correlating said bicoherence array with a control bicoherence array in order to produce a cross-correlation coefficient, determining the reduction in the bicoherence cross-correlation coefficient in the frequency pairs in the bands between 0.05 to 200 Hz;

determining the magnitude of induced ischemia on the basis of the greater the reduction in the bicoherence cross-correlation coefficient in the frequency pairs between 0 to 200 Hz from a base cross-correlation coefficient, the greater the magnitude of the induced ischemia.

18. The method of noninvasively detecting heart disorders of claim 17 further comprising the step of:

after producing said cross-correlation coefficient, displaying the cross-correlation coefficient of the bicoherence array on a grid, said grid having an area representing a location probed by each electrode with each area containing a cross-correlation coefficient of the bicoherence array.

19. The method of noninvasively detecting heart disorders of claim 1 wherein said step of utilizing said bispectral parameters to quantify the contribution to overall cardiac physiologic function provided by the region probed by said surface electrode comprises the steps of:

correlating said bispectral density array with a control bispectral density array in order to produce a cross-correlation coefficient, determining the reduction in the bispectral density cross-correlation coefficient in the frequency pairs in the bands between 0 to 100 Hz and 200 to 300 Hz;

determining the heterogeneity in conduction and repolarization on the basis that the greater the increase in the bispectral density cross-correlation coefficient in said frequency pairs, the greater the heterogeneity.

20. A system for noninvasively detecting heart disorders that affect cardiac electric activity, said system comprising means for acquiring electrocardiographic signals from a surface of the body of a subject being analyzed means for determining a waveform template representing a normal QRST waveform in said subject;

means for selecting a number of complexes that match said waveform template;

means for storing said number of complexes for processing;

means for computing bispectral parameters from said stored number of selected complexes.

21. The system for noninvasively detecting heart disorders of claim 20 further comprising a plurality of surface electrodes that are positionable on a surface of the body of a subject being analyzed.

22. The system for noninvasively detecting heart disorders of claim 20 wherein said means for acquiring electrocardiographic signals comprises a surface electrode that is positionable on the surface of the body of a subject being analyzed.

23. The system for noninvasively detecting heart disorders of claim 20 wherein said means for acquiring electrocardiographic signals comprises:

a plurality of surface electrodes mounted on the surface of the body of the subject being analyzed;

means of providing electrosurgery protection including a radio frequency filter for limiting radio frequency current to patient leads;

means for providing defibrillator protection for limiting the current to patient leads during a defibrillator discharge;

means for amplifying signals acquired by electrode leads;

means for multiplexing said amplified signals so as to provide one signal at a time, said one signal being fed to an analog to digital convertor;

means for providing said acquired digital signals in a serial fashion to said system for further processing.

24. The system for noninvasively detecting heart disorders of claim 20 wherein said means for computing bispectral parameters comprises a computer system including:

means for receiving data in a serial fashion from said means for acquiring electrocardiographic signals;

an array processor, connected to said means for storing, for performing simultaneous arithmetic calculations on an array of data;

a math coprocessor, connected to said means for storing, for calculating graphic modalities;

processor means for controlling input and output to peripheral devices connected to said means for computing.

25. A method of noninvasively detecting heart disorders that affect cardiac electrical activity, said method comprising the steps of:

acquiring electrocardiographic signals from a surface of the body of a subject being analyzed;

applying bispectral analysis to QRST complexes of said acquired electrocardiographic signal for a plurality of consecutive beats of the heart of the subject in order to quantity physiologic function that indicate heart disorders.

* * * * *